(12) United States Patent
Brooks et al.

(10) Patent No.: US 10,552,791 B2
(45) Date of Patent: Feb. 4, 2020

(54) SYSTEMS AND METHODS FOR MONITORING AND RECONCILING INVENTORY

(71) Applicant: Walmart Apollo, LLC, Bentonville, AR (US)

(72) Inventors: Cristy C. Brooks, Cassville, MO (US); Greg A. Bryan, Centerton, AR (US); Todd D. Mattingly, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days.

(21) Appl. No.: 15/790,305

(22) Filed: Oct. 23, 2017

(65) Prior Publication Data

US 2018/0114184 A1 Apr. 26, 2018

Related U.S. Application Data

(60) Provisional application No. 62/411,852, filed on Oct. 24, 2016.

(51) Int. Cl.
*G06Q 10/08* (2012.01)
*G01G 23/18* (2006.01)
(Continued)

(52) U.S. Cl.
CPC ........... *G06Q 10/087* (2013.01); *G01G 23/18* (2013.01); *G06K 7/10544* (2013.01); *G06K 9/20* (2013.01); *A61B 5/0404* (2013.01)

(58) Field of Classification Search
CPC .... G06Q 10/087; G06K 7/10544; G06K 9/20; G06K 9/00624; G06K 2209/17; G01G 23/18; G01G 19/42; A61B 5/0404
See application file for complete search history.

(56) References Cited

U.S. PATENT DOCUMENTS 7,518,068 B2 4/2009 Green
7,596,426 B2 9/2009 McGrady
(Continued)

FOREIGN PATENT DOCUMENTS

EP 1901215 3/2008
WO 2001067356 9/2001

OTHER PUBLICATIONS

PCT; App. No. PCT/US2017/057834; International Search Report and Written Opinion dated Jan. 4, 2018.

*Primary Examiner* — Sonji N Johnson
(74) *Attorney, Agent, or Firm* — Fitch, Even, Tabin & Flannery LLP (57) ABSTRACT

In some embodiments, apparatuses and methods are provided herein useful to monitoring and reconciling inventory. In some embodiments, there is provided a system including: an inventory location for one type of merchandise item intended for the inventory location; a first sensor configured to collect data regarding the presence of the merchandise item at the inventory location; a second sensor configured to collect identification data of the merchandise item at the inventory location; a memory configured to store the identification data; a database including identification information corresponding to the merchandise item intended for the inventory location; a control circuit configured to: compare the identification data collected by the second sensor with the identification information from the database corresponding to the merchandise item; verify that the identification data from the second sensor corresponds to the identification information from the database; and calculate a quantity of inventory at the inventory location.

15 Claims, 7 Drawing Sheets

(51) Int. Cl.
*G06K 7/10* (2006.01)
*G06K 9/20* (2006.01)
A61B 5/0404 (2006.01)

(56) References Cited

U.S. PATENT DOCUMENTS

| | | |
|---|---|---|
| 7,603,291 B2 | 10/2009 | Raiyani |
| 7,650,298 B2 | 1/2010 | Godlewski |
| 7,775,130 B2 | 8/2010 | Harish |
| 8,091,782 B2 | 1/2012 | Cato |
| 8,299,920 B2 | 10/2012 | Hamm |
| 9,024,755 B2 | 5/2015 | Fuhr |
| 9,123,018 B2 | 9/2015 | Gentile |
| 9,165,278 B2 | 10/2015 | Vasantham |
| 2006/0071774 A1 | 4/2006 | Brown |
| 2008/0035727 A1 | 2/2008 | Stanzel |
| 2010/0070365 A1 | 3/2010 | Siotia |
| 2011/0153466 A1 | 6/2011 | Harish |
| 2013/0117053 A2 | 5/2013 | Campbell |
| 2014/0195374 A1 | 7/2014 | Bassemir |
| 2014/0201041 A1 | 7/2014 | Meyer |
| 2014/0201042 A1 | 7/2014 | Meyer |
| 2015/0041616 A1* | 2/2015 | Gentile ................ G06Q 10/087 248/550 |
| 2016/0048798 A1 | 2/2016 | Meyer |
| 2016/0260161 A1 | 9/2016 | Atchley |
| 2017/0177969 A1* | 6/2017 | Zaremski ........... G06K 9/00771 |
| 2017/0193434 A1* | 7/2017 | Shah .................. G06K 9/00664 |
| 2017/0318422 A1* | 11/2017 | Kokkonen ........... H04W 4/023 |
| 2018/0181906 A1* | 6/2018 | Baduge .................. H04W 4/02 |

* cited by examiner

SYSTEMS AND METHODS FOR MONITORING AND RECONCILING INVENTORY

CROSS-REFERENCE TO RELATED APPLICATION

This application claims the benefit of U.S. Provisional Application No: 62/411,852, filed Oct. 24, 2016, which is incorporated by reference in its entirety herein.

TECHNICAL FIELD

This invention relates generally to monitoring inventory, and more particularly, to monitoring and reconciling inventory at a shopping facility.

BACKGROUND

In retail settings, one challenge is maintaining an accurate count and record of on-hand inventory in a shopping facility. It is desirable to provide an arrangement of sensors to monitor merchandise on or about a shelf in a shopping facility where the merchandise is intended for sale to customers. The sensor arrangement monitors the shelf and can provide an alert for re-stocking if the inventory on the shelf falls below a predetermined amount.

However, it has been found that on-hand inventory records at shopping facilities may still be understated or overstated. This inaccuracy can result in several ways. For example, some of the merchandise on a shelf may not be intended for that shelf, such as when a sales associate or customer puts the wrong merchandise on the shelf. Also, some of the merchandise may be unaccounted for in the back rooms or storage areas of the shopping facility. Accordingly, it is desirable to develop systems and methods using sensors to monitor and verify merchandise in the shopping facility and to reconcile the merchandise count with on-hand inventory records at the shopping facility.

BRIEF DESCRIPTION OF THE DRAWINGS

Disclosed herein are embodiments of systems, apparatuses and methods pertaining to monitoring and reconciling inventory. This description includes drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein useful to monitoring and reconciling on-hand inventory at a shopping facility. In some embodiments, there is provided a system for monitoring inventory including: a first inventory location configured to contain a plurality of one type of merchandise item intended for the first inventory location; a first sensor disposed at the first inventory location and configured to collect data regarding the presence of the merchandise item at the first inventory location; a second sensor configured to collect identification data of the merchandise item at the first inventory location; a memory configured to store the identification data collected by the second sensor; a database including identification information corresponding to the merchandise item intended for the first inventory location; a control circuit operatively coupled to the first and second sensors and in communication with the database, the control circuit configured to: compare the identification data collected by the second sensor with the identification information from the database corresponding to the merchandise item; verify that the identification data from the second sensor corresponds to the identification information of the merchandise item from the database; and calculate a quantity of inventory at the first inventory location based on the data from the first sensor.

In one form, the first inventory location comprises a shelf at a shopping facility. Further, the first sensor may include a plurality of weight sensors arranged at the first inventory location to collect weight data regarding the merchandise item at predetermined positions of the first inventory location. In addition, the first sensor may include a plurality of individual strips defining a grid and extending along a bottom surface of the first inventory location.

In one form, the second sensor may include a scanning device including at least one of a barcode reader, an RFID reader, an NFC reader, a laser imager, an optical sensor, an image recognition device, or a text capture device configured to read corresponding identification data. Further, the second sensor may include a scanning device configured to systematically collect identification data at a plurality of inventory locations. In addition, control circuit may be configured to: compare the identification data collected by the second sensor at the plurality of inventory locations with the identification information of the merchandise item from the database; determine if any identification data at the plurality of inventory locations correspond to the identification information of the merchandise item from the database; and determine that the merchandise item is located at an inventory location other than or in addition to the first inventory location. Also, in the system, the identification data may be images; the second sensor may be configured to systematically capture images at the plurality of inventory locations; and the control circuit may be configured to: compare the images captured by the second sensor at the plurality of inventory locations with at least one image of the merchandise item from the database; and determine if any images at the plurality of inventory locations correspond to the at least one image of the merchandise item from the database. Moreover, the identification information of the merchandise item from the database may include a planogram.

In one form, the database may contain weight data for the merchandise item intended for the first inventory location, and the control circuit may be configured to calculate the quantity of inventory at the first inventory location based on the weight data for the merchandise item and based on the data from the first sensor at the first inventory location. Further, the control circuit may be: communicatively coupled to an on-hand inventory database containing an on-hand inventory record for the merchandise item; configured to compare the on-hand inventory record to the calculated quantity of inventory at the first inventory location; and configured to adjust the on-hand inventory record. In addition, the control circuit may be configured: to receive additional data from one or more sources other than the first and second sensors regarding the inventory of the merchandise item intended for the first inventory location; to compare the on-hand inventory record to the additional data regarding the inventory of the merchandise item; and to adjust the on-hand inventory record based on the additional data. Also, the additional data may include at least one of: data from handheld scanners reading merchandise information at the first inventory location, imaging data from imaging equipment mounted at or near the first inventory location, sales or receipts of the merchandise item intended for the first inventory location, and feedback from customers regarding the quantity of the merchandise item at the first inventory location or the absence of the merchandise item from the first inventory location. Moreover, the system may further include a visual alert indicator actuated by the control circuit when the calculated quantity of inventory at the first inventory location is below a predetermined amount.

In another form, there is provided a method for monitoring inventory including: depositing a plurality of one type of merchandise item at a predetermined first inventory location; by a first sensor, collecting data regarding the presence of the merchandise item at the predetermined first inventory location; by a second sensor, collecting identification data of the merchandise item at the predetermined first inventory location; storing the identification data collected by the second sensor; by a control circuit: comparing the identification data collected by the second sensor with identification information of the merchandise item from a database; verifying that the identification data from the second sensor corresponds to the identification information of the merchandise item from the database; and calculating a quantity of inventory at the predetermined first inventory location based on the data from the first sensor.

Figure 1:
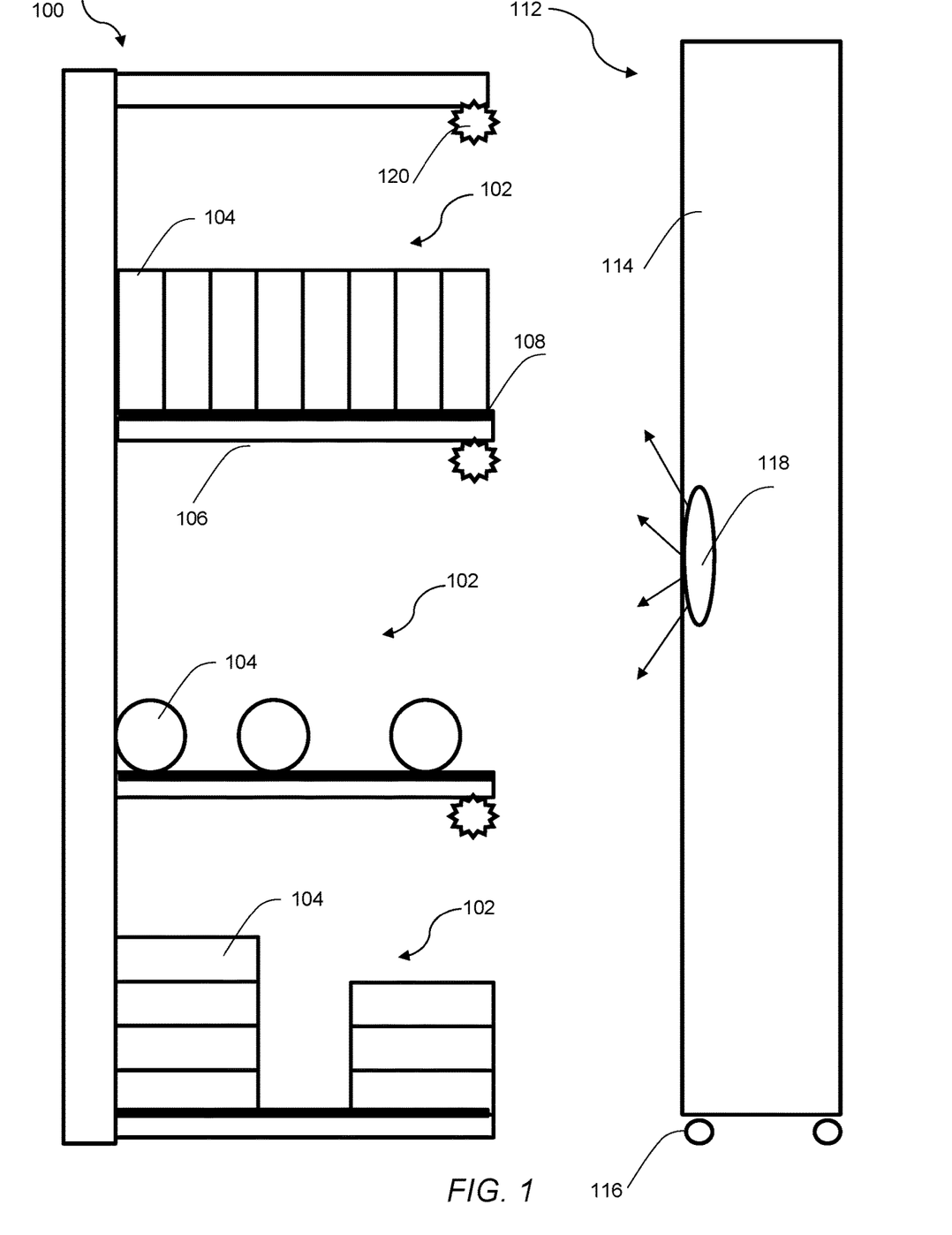
FIG. 1 is a schematic representation in accordance with some embodiments.
Figure 2:
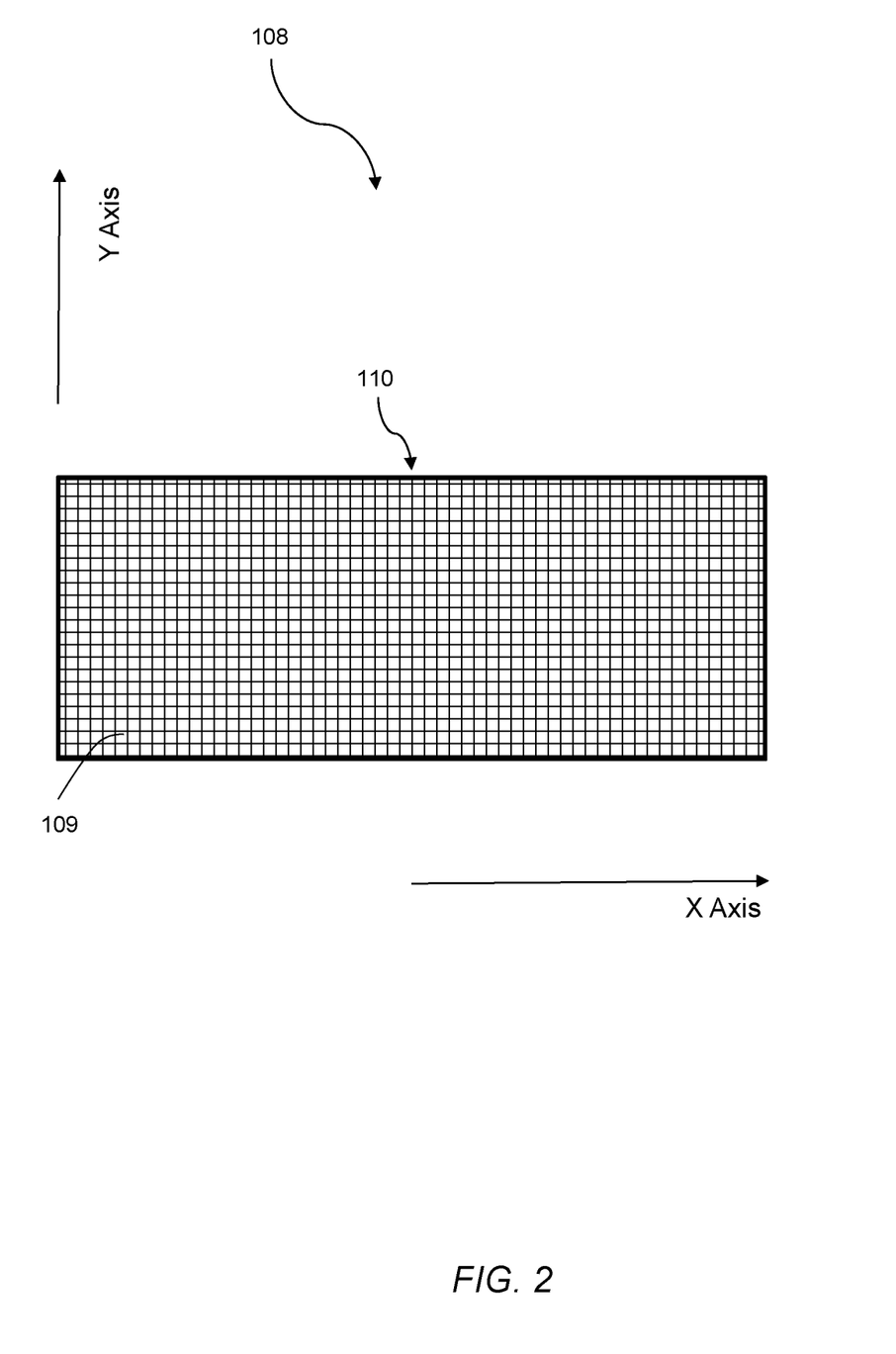
FIG. 2 is a schematic representation in accordance with several embodiments.

As shown in FIGS. 1 and 2, there is provided a system 100 for monitoring inventory at a shelf or other inventory location at a shopping facility. It is generally contemplated that there are, at least, two sensors for measuring data at the shelf. As addressed further below, the combination of sensors allows for verification of the merchandise at the shelf and calculation of the inventory at the shelf.

In FIG. 1, there are shown three inventory locations, or shelves, 102 supporting various types of merchandise 104. Each shelf or inventory location is generally arranged to hold one type of merchandise item 104 intended for that location. For each shelf 102, the bottom surface 106 includes a first sensor 108 collecting data regarding the presence of the merchandise item 104 at the location. In one form, it is generally contemplated that this first sensor 108 is selected to measure weight/pressure. More particularly, in one form it is contemplated that the first sensor 108 includes multiple weight sensors, or pressure-sensitive sensors, that detect the weight of the merchandise 104 on the shelf 102 being supported by the bottom surface 106.

As can be seen from FIG. 2, the first sensor 108 may be arranged as multiple individual sensor strips (generally square in shape) 109 extending along the bottom surface 106 and defining a sensing grid or matrix 110. In some forms, it is contemplated that the sensor strips 109 may be built into the shelf 102 itself or may be incorporated into a liner or mat supported by the bottom surface 106. Although the first sensor 108 is shown as arranged to form a grid 110, it should be evident that many other arrangements are possible. For example, the first sensor 108 may also be in the form of lengthy rectangular sensor strips extending along either the x-axis or y-axis in FIG. 2. It is generally desirable to select the first sensor 108 such that the data regarding the merchandise 104 over the entire bottom surface 106 can be detected, such as, for example, detecting pressure or weight indicating the presence or absence of merchandise at each individual sensor strip 109. In one form, the bottom surface 106 is covered with an appropriate array of sensor strips 109 with sufficient discrimination and resolution so that, in combination, the sensor strips 109 are able to identify the quantity (and possibly the type) of merchandise 104 on the shelf 102.

As shown in FIG. 1, there is also a second sensor 112 that collects identification data regarding the merchandise item 104 at the shelf 102. In one form, it is contemplated that the second sensor 112 may be a portable robot scanning device 114 that may be supported by wheels 116 and move up and down the aisles of a shopping facility. The portable robot scanning device 114 may include some sort of reader 118 for reading the identification data at the shelf 102. In this form, as the portable robot scanning device 114 moves up and down the aisles, it may be configured to direct its reader 118 so that it collects identification data from all of the shelves 102 that its reader 118 is facing.

The reader 118 and identification data may any of various types. For example, the reader 118 may be a barcode reader, an RFID reader, an NFC reader, a laser imager, an optical sensor, an image recognition device, or a text capture device. The identification data corresponds to the type of reader 118 used and may constitute a barcode; an RFID tag; an NFC tag; text, logos, graphics, and/or symbols from the merchandise item 104; the shape and/or size of the merchandise item 104; or any other type of identification data located on the merchandise item 104 or at the shelf 102. It should be understood that reference to reading identification data from the merchandise item 104 includes reading such identification data from any packaging of the merchandise item 104.

In one form, it is contemplated that the portable robot scanning device 114 may have a barcode reader. The barcode reader may read barcodes on individual merchandise items 104 on the shelf 102 and/or may read a barcode on the shelf 102. In other words, the barcode reader may scan product and/or shelf barcode labels with universal product codes (UPCs).

In another form, it is contemplated that the portable robot scanning device 114 may have some sort of optical reader or image capture device (in addition to or in lieu of a barcode or other reader). In this form, the second sensor 112 may be configured to capture images of at least one merchandise item 104 on the shelf 102. As addressed further below, these images serve as identification data regarding the merchandise 104.

Each shelf 102 may also be associated with a visual alert indicator 120, which may generally include some sort of flashing light or other lighting assembly. The indicator 120 may help workers/sales associates identify where to restock and/or direct customers to a product. When restocking/ activity is to occur, the indicator 120 may be activated. Additionally or alternatively, the indicator 120 may be activated in response to detecting restocking. Sensors may further detect the presence of customers and/or workers (e.g., motion sensors) and activate the indicator(s) 120 when the customer/worker is within a threshold distance (e.g., flash light). In one form, the visual alert indicator 120 is generally disposed at or near each shelf 102 and may indicate a low inventory condition. This low inventory condition is based on the data from the combination of sensors, as described below.

Figure 3:
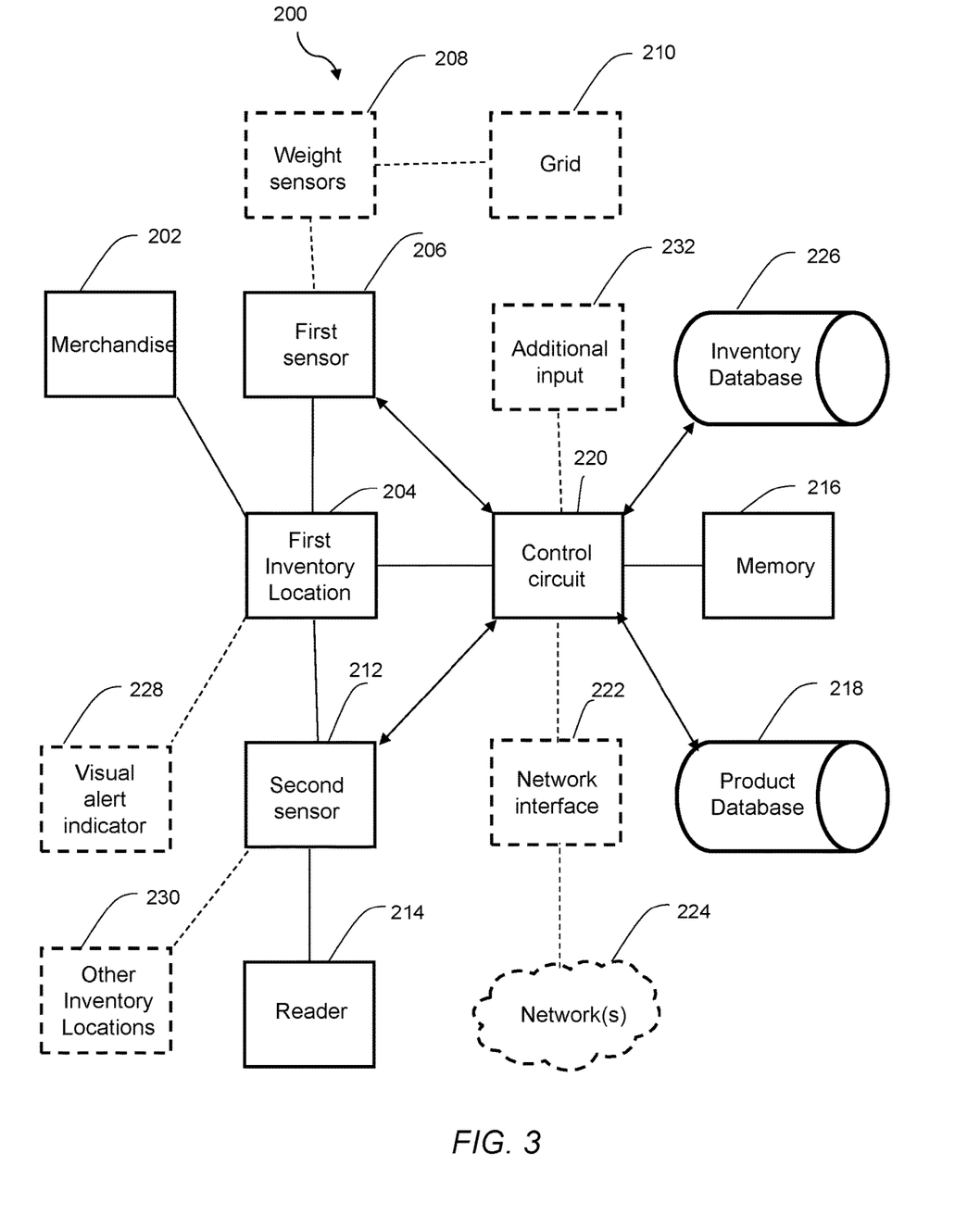
FIG. 3 is a block diagram in accordance with some embodiments.

Referring to FIG. 3, there is shown a block diagram illustrating various components of a system 200. The system 200 generally includes, at least, two sensors that monitor a first inventory location (or shelf) intended to hold merchandise. Based on one sensor, the system 200 verifies that identification data from the first inventory location corresponds to, or matches, identification information regarding the merchandise intended for the first inventory location. Based on another sensor, the system 200 calculates inventory at the first inventory location and may compare it to an on-hand inventory record.

It is generally contemplated that one type of merchandise 202 is intended for a specific first inventory location 204. For example, in the context of a shopping facility, different types of merchandise may be intended for specific shelves and aisles of the shopping facility. In other words, the first inventory location 204 is configured to contain a plurality of one type of merchandise item 202 intended for the first inventory location 204. It is generally contemplated that various types of merchandise 202 and inventory locations 204 are suitable for the system 200 herein.

A first sensor 206 is disposed at or near the first inventory location 204 and is configured to collect data regarding the presence of the merchandise item 202 at the first inventory location 204. It is generally contemplated that this first sensor 206 will collect data used to calculate the quantity of merchandise 202 at this first inventory location 204. In one form, the first sensor 206 may collectively include a plurality of weight sensors 208 arranged at the first inventory location 204 to collect weight data regarding the merchandise item 202 at certain positions of the first inventory location 204. The weights sensors 208 may be arranged as a plurality of individual strips, or squares, defining a grid 210 and extending along a bottom surface of the first inventory location 204. In this form, the first sensor 206 can detect the weight or pressure at different parts of the first inventory location 204, and this weight data can be used to calculate the quantity of merchandise at the location 204. For example, the system 200 may use known weight information for an individual merchandise item 202 in making this calculation. Further, as described further below, the weight measurements may indicate that the first inventory location 204 includes one or more merchandise items that are of the wrong type and that have been improperly placed at the location 204.

A second sensor 212 is configured to collect identification data of the merchandise item 202 at the first inventory location 204. In one form, it is contemplated that the second sensor 212 may be in the form of a portable robot scanning device that may move up and down the aisles of a shopping facility to scan the identification data at multiple shelves. As described above, it is generally contemplated the second sensor 212 may use any of various types of readers 214 to scan corresponding identification data, including, for example, barcode readers, RFID readers, NFC readers, laser imagers, optical sensors, image recognition devices, or text capture devices.

In one form, the reader 214 may be a barcode reader. In this form, for example, the barcode reader 214 may scan a shelf barcode indicating generally the type of merchandise on the shelf and/or it may scan barcodes on all of the individual merchandise items 202 themselves that are visible to the reader 214. By scanning the merchandise items 202, it can be determined if there is an improper merchandise item 202. For example, a sales associate or customer may have placed or replaced a product on the shelf that does not belong on that shelf. In this manner, it may be determined that the inventory count of merchandise on the shelf may be incorrect based on the presence of unintended products.

The system 200 may also include a memory 216 configured to store the identification data collected by the second sensor 212. This memory 216 may be of various types. It may be part of a unitary structure that defines both the second sensor 212 and memory 216. For example, the second sensor 212, reader 214, and memory 216 (in the form of a local memory storage device) may all be components of a portable robotic scanning device. Alternatively, the memory 216 may be more remote from the second sensor 212, and the identification data may be transmitted to memory 216.

The system 200 further has a product database 218 including identification information corresponding to the merchandise item 202 intended for the first inventory location 204. It is generally contemplated that the system 200 will compare the identification data from the second sensor 212 with the identification information in the product database 218 for the merchandise item 202 that is supposed to be on the shelf. So, for example, in the case of a barcode, the system 200 compares the barcode at the first inventory location 204 or on the actual products to the known barcode in the product database 218. As another example, in the case of image recognition, the system 200 compares the images of one or more merchandise items 202 at the first inventory location 204 that are visible to the reader 214 with known images of the merchandise item 202 from an image database 218. In this example, it is contemplated that the images may correspond to parts or all of the merchandise item 202. The images collected by the second sensor 212 may include the general overall physical dimensions and shape of the product and/or symbols and/or text from the product. These images may be compared to corresponding images showing physical dimensions, shape, symbols, and/or text from the image database 218. In one form, the identification information of the merchandise item 202 from the image database 218 may be a planogram that shows a general layout of one or more types of specific retail products on store shelves.

The system 200 also includes a control circuit 220 that is configured to receive data from the first and second sensors 206, 212. In this context, the term control circuit 220 refers broadly to any microcontroller, computer, or processor-based device with processor, memory, and programmable input/output peripherals, which is generally designed to govern the operation of other components and devices. It is further understood to include common accompanying accessory devices, including memory, transceivers for communication with other components and devices, etc. These architectural options are well known and understood in the art and require no further description here. The control circuit 220 may be configured (for example, by using corresponding programming stored in a memory as will be well understood by those skilled in the art) to carry out one or more of the steps, actions, and/or functions described herein.

By one approach, the control circuit 220 operably couples to the memory 216. This memory 216 may be integral to the control circuit 220 or can be physically discrete (in whole or in part) from the control circuit 220 as desired. This memory 216 can also be local with respect to the control circuit 220 (where, for example, both share a common circuit board, chassis, power supply, and/or housing) or can be partially or wholly remote with respect to the control circuit 220 (where, for example, the memory 216 is physically located in another facility, metropolitan area, or even country as compared to the control circuit 220).

This memory 216 can serve, for example, to non-transitorily store the computer instructions that, when executed by the control circuit 220, cause the control circuit 220 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

In one form, the control circuit 220 also operably couples to a network interface 222. So configured, the control circuit 220 can communicate with other elements (both within the system 200 and external thereto) via the network interface 222. Network interfaces, including both wireless and non-wireless platforms, are well understood in the art and require no particular elaboration here. This network interface 222 can compatibly communicate via whatever network or networks 224 may be appropriate to suit the particular needs of a given application setting. It is also contemplated that users may remotely access the network or networks 224 via mobile devices and applications. Both communication networks and network interfaces are well understood areas of prior art endeavor and therefore no further elaboration will be provided here in those regards for the sake of brevity.

As can be seen from FIG. 3, the control circuit 220 is operatively coupled to the first and second sensors 206, 212 and in communication with the product database 218. The control circuit 220 compares the identification data collected by the second sensor 212 with the identification information from the product database 218, verifies that the identification data from the second sensor 212 corresponds to the identification information for the merchandise item 202 from the database 218, and calculates the quantity of inventory at the first inventory location 204 based on the data from the first sensor 206. For example, in one simple form, the control circuit 220 may take the total weight measured by the first sensor 206 at the first inventory location 204, may access the known weight for one merchandise item 202 from the product database 218, and may divide the two values to calculate a quantity. However, it should be understood that there are various other ways to calculate quantity using the first sensor 206, especially where the first sensor 206 is collectively composed of a grid of weight sensors each with sufficient discrimination and resolution so that, in combination, the sensors may be able to identify the quantity and possibly the type of merchandise 202 at various positions of the first inventory location 204. As described further below, the calculated inventory quantity may be compare to an on-hand inventory record in an inventory database 226.

In one form, if the inventory calculated falls below a certain minimum amount, the control circuit 220 may activate a visual alert indicator 228 at or near the first inventory location 204. The visual alert indicator 228 may be, for example, a lamp, a flashing light, or any generally known lighting assembly. In one form, the indicator 228 may be used to provide notice to a sales associate, who may then restock the merchandise 202 at the first inventory location 204, although it also may be used to provide different alerts.

In one form, it is contemplated that the rest of a shopping facility may be scanned systematically for the presence of the type of merchandise item 202. Under one approach, the second sensor 212 may include a scanning device configured to systematically collect identification data of merchandise items at a plurality of inventory locations 230 (in addition to the first inventory location 204). For example, as described above, the second sensor 212 may be a portable robot scanning device that can move up and down the aisles of a shopping facility and can navigate through a back room or other storage areas of the shopping facility. In this manner, the second sensor 212 may identify and locate other caches of merchandise items 202 of the type intended for the first inventory location 204 that have been "lost track of" in the shopping facility.

In this form, the control circuit 220 may be configured to: compare the identification data collected by the second sensor 212 at the plurality of inventory locations 230 with the identification information of the merchandise item 202 from the product database 218; determine if any identification data at the plurality of inventory locations 230 correspond to the identification information of the merchandise item 202 from the database 218; and determine that the merchandise item 202 is located at an inventory location 230 other than or in addition to the first inventory location 204. If additional quantities of merchandise 202 are located at other parts of a shopping facility, other sensors may be used to calculate the quantity at these other locations 230, or a sales associate may manually count the quantity at these other locations 230. In this manner, the system 200 allows for a systematic approach for determining if the actual quantity of a merchandise item 202 throughout an entire shopping facility is inconsistent with the on-hand record in an inventory database 226. This systematic approach helps address the issue of overstated inventory records ("phantom inventory") or understated inventory records (such as unknown caches of inventory in a back room location) that may result from inaccurate manual counts of merchandise item 202.

In one form, it is contemplated that the second sensor 212 may collect identification data in the form of images of merchandise items, which may be collected throughout the shopping facility. For example, the second sensor 212 may be a portable robot scanning device with image recognition capability that captures images of inventory locations 230 as it navigates through the shopping facility. In other words, the second sensor 212 may be configured to systematically capture images of merchandise items at the inventory locations 230. The control circuit 220 may be configured to: compare the images captured by the second sensor 212 at the inventory locations 230 with at least one image of the merchandise item 202 from the product database 218; and determine if any images at the inventory locations 230 correspond to the at least one image of the merchandise item 202 from the database 218. Again, the images may be in the form of any identifying portion of the merchandise item 202 (including any packaging), such as the physical shape, text, symbols, logos, graphics, or portions thereof.

In another form, the control circuit 220 may receive additional input/data 232 that may be considered to adjust the on-hand inventory record. More specifically, the control circuit 220 may be configured: to receive additional data 232 from one or more sources other than the first and second sensors 206, 212 regarding the inventory of the merchandise item 202 intended for the first inventory location 204; to compare the on-hand inventory record to the additional data 232 regarding the inventory of the merchandise item 202; and to adjust the on-hand inventory record based on the additional data 232. Some of these additional sources and additional data 232 are described further below.

Further, it should be understood that the system 200 may include a variety of arrangements of databases. For example, the product database 218 and the inventory database 226 may form one comprehensive database. Alternatively, each of the product database 218 and the inventory database 226 may be sub-divided into small database components. As should evident, the databases may be organized in any of various ways, such as, for example, to be arranged as a single comprehensive database or to be arranged by multiple databases and/or sub-databases. This disclosure is generally intended to encompass any of these various manners of organization of databases.

Figure 4:
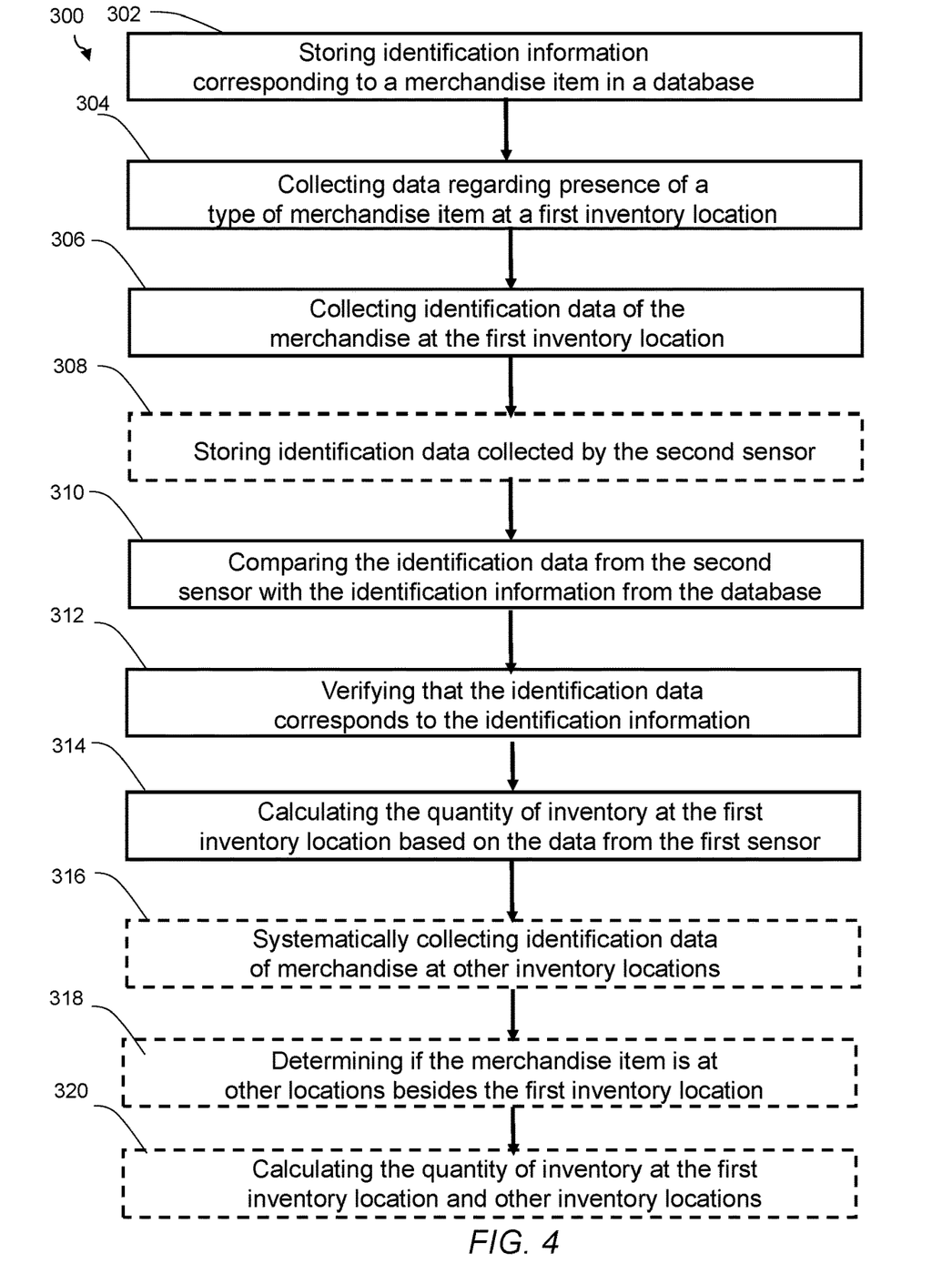
FIG. 4 is a flow diagram in accordance with several embodiments.

Referring to FIG. 4, there is a shown a process 300 that may use some of the components of systems 100 and 200. It is generally contemplated that process 300 uses, at least, two sensors collecting data at or near a first inventory location, or shelf. In this process 300, one of the sensors may collect data at other inventory locations to determine if merchandise of the type intended for the first inventory location may also be present at other inventory locations.

At block 302, identification information corresponding to the merchandise item is stored in a product database. Generally, it is contemplated that identification information for a number of different merchandise items may be stored. As described above, this identification information may be of any of various types of information, such as a barcode; an RFID tag; an NFC tag; text, logos, graphics, and/or symbols from the merchandise item; the shape and/or size of the merchandise item; or any other type of identification data located on the merchandise item or at the shelf. In one form, it is contemplated that the identification information may be some sort of image information stored in an image database. The identification information stored in the database serves as a model for comparison for the identification data collected by the second sensor.

At block 304, data is collected regarding the presence of a type of merchandise item at a first inventory location. The data may be collected by a first sensor, as described above. In one form, this first sensor may include an arrangement of weight sensors on a bottom surface at the first inventory location.

At block 306, identification data is collected regarding the nature of the merchandise at the first inventory location. In one simple form, this collection may involve scanning an identification code (such as a barcode) at the first inventory location. In another form, this collection may involve scanning identification codes (such as UPC barcodes) on the merchandise items themselves. Alternatively, this collection may involve a second sensor having image recognition capability that collects image data of merchandise items that are visible to the second sensor. At block 308, the identification data may be stored.

At blocks 310-314, the identification data is evaluated, and the quantity of merchandise at the first inventory location is calculated. At block 310, the identification data from the second sensor is compared with the identification information for the merchandise item from the database. At block 312, it is verified that the identification data corresponds to the identification information. In other words, it is generally determined that there is a match between the identification data and the identification information. This match determines that the correct inventory location is being monitored and also may determine that one or more incorrect merchandise items may have been deposited at the first inventory location. At block 314, the quantity of inventory at the first inventory location may be calculated based on the data from the first sensor. For example, the first sensor may use weight data to calculate quantity.

At blocks 316-320, it is contemplated that other inventory locations may be checked for additional inventory of the merchandise item. At block 316, identification data of merchandise may be systematically collected at other inventory locations. In one form, it is contemplated that an automated second sensor, such as in the form of a portable robot scanning device, may be used to collect this identification data. At block 318, it is determined whether the merchandise item is at other inventory locations by determining if there is a match between the identification data and the identification information in the database. At block 320, the quantity of inventory at the first inventory location and at other inventory locations may be calculated. It is generally contemplated that, if the merchandise item is located at other inventory locations, the quantity of the merchandise item at these other inventory locations may be calculated either manually or through the use of other sensors. The quantity of merchandise items at other inventory locations may be added to the quantity at the first inventory location to determine an overall inventory, such as throughout an entire shopping facility.

Figure 5:
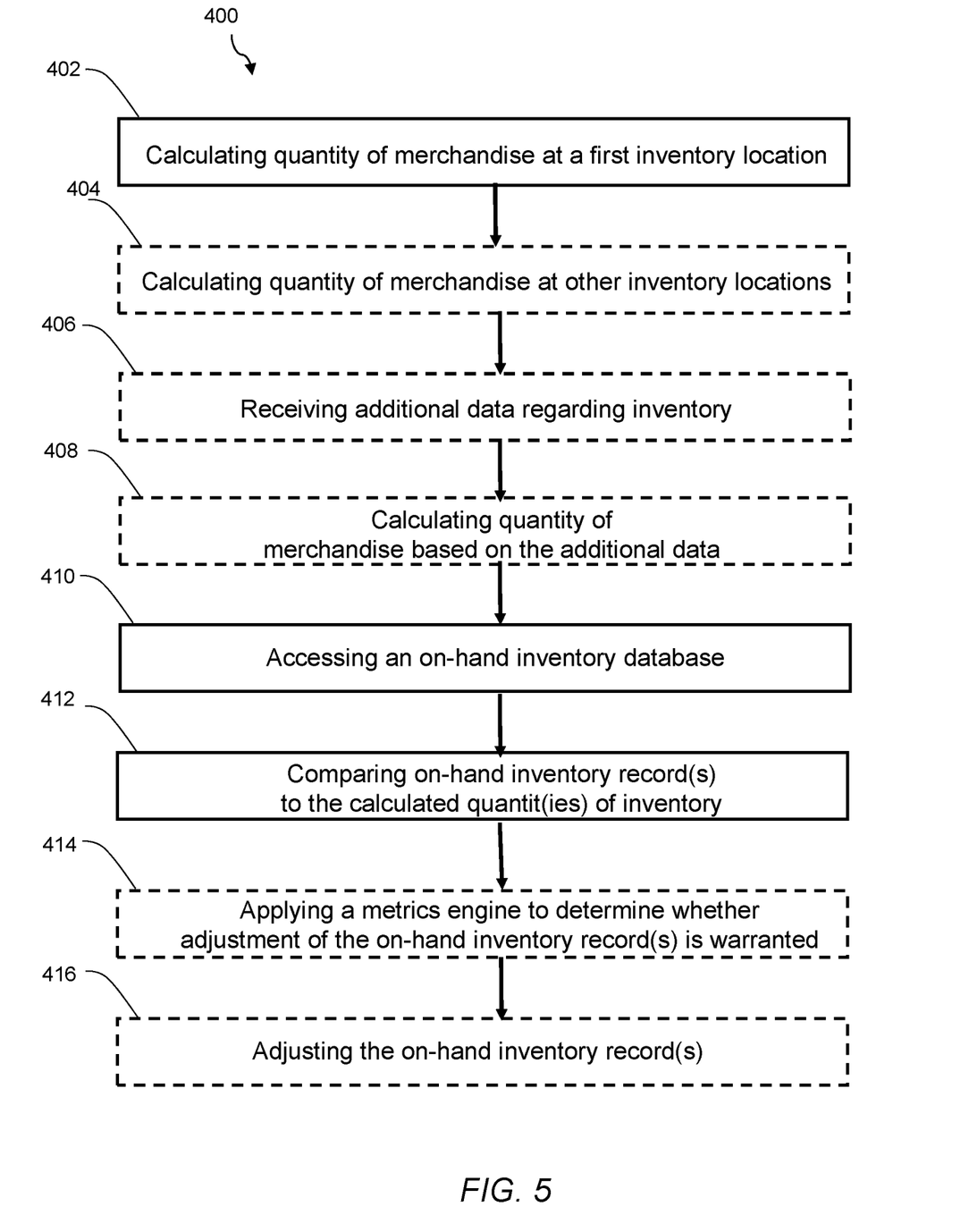
FIG. 5 is a flow diagram in accordance with some embodiments.

Referring to FIG. 5, there is shown a process 400 for monitoring/tracking inventory that may use some of the components of systems 100 and 200 and steps of process 300. This process 400 is generally intended to include several possible approaches for tracking inventory and reconciling a measured or determined quantity with an on-hand inventory record in an inventory database. As described below, these approaches may use several data sources for collecting data and a metrics engine in determining whether to an adjust inventory record.

At block 402, the quantity of merchandise may be measured and/or calculated at a first inventory location. It is contemplated that a merchandise item is specifically intended for this first inventory location. It is also generally contemplated that this quantity may be calculated in the manner described above using first and second sensors.

At block 404, the quantity of merchandise may be measured and/or calculated at other inventory locations. In one form, it is contemplated that a second sensor may be used to systematically identify these other inventory locations, such as described above. This step may be an optional approach. Other data sources may be used to collect additional data regarding merchandise inventory, such as at a shopping facility.

At block 406, additional data regarding inventory may be collected and received, such as from sources other than the first and second sensors. For example, it is contemplated that the additional data may include data from handheld scanners reading merchandise information at the first inventory location or other inventory locations (such as may be gathered by a sales associate), imaging data from imaging equipment mounted at or near the first inventory location (such as a stationary camera mounted at or about a shelf that may detect gaps in the merchandise item on the shelf or an incorrect type of product on the shelf), sales and receipts of the merchandise item intended for the first inventory location (such as sales records and shipment receipt records suggesting an inconsistency with inventory records), and feedback from customers regarding the quantity of the merchandise item at the first inventory location or the absence of the merchandise item from the first inventory location (such as a customer stating that no merchandise was present on the shelf or that the wrong type of merchandise was available on the shelf). It is contemplated that this step may be an optional step and may be performed before or after other steps shown in FIG. 5.

At block 408, the quantity of merchandise may be calculated or re-calculated based on the additional data. This calculation or re-calculation may occur at the first inventory location and/or the other inventory locations. For example, a manual handheld scan or a customer comment may indicate that a low number of merchandise items (or the wrong type of merchandise items) are present at the first inventory location, and the additional data may be used to calculate or re-calculate the measured quantity of merchandise at the first inventory location. As another example, sales records may indicate a certain quantity at other inventory locations that is inconsistent with measured or calculated data from a second sensor, which may warrant re-calculation of quantity at the other inventory locations.

At block 410, on-hand inventory record(s) may be accessed in an inventory database. These inventory record(s) may constitute the official counts or records of merchandise inventory at the first location, the other inventory locations, and/or throughout a shopping facility. At block 412, these on-hand inventory records(s) are compared to corresponding measured or calculated quantities of merchandise inventory at the first location, the other inventory locations, and/or throughout a shopping facility. The inventory record(s) and measured/calculated quantities are compared to determine any inconsistencies and to potentially reconcile the record(s) with actual quantities.

At block 412, a metrics engine may be applied to determine when adjustment of the on-hand inventory record(s) is warranted. For example, it may be desirable to repeat some of the measurements/calculations before adjusting the record(s). In other words, the metrics engine may include a rule requiring repeating, a certain number of times, the steps of collecting data by a first sensor, collecting identification data by a second sensor, storing identification data, comparing identification data, verifying identification data, calculating the quantity of inventory (such as at both the first inventory location and other inventory locations), communicating with an on-hand inventory database, and comparing an on-hand inventory record to a calculated quantity of inventory, and if there is a discrepancy each time, adjusting the on-hand inventory record. For example, if a measurement is performed several times in a predetermined time interval (such as one week) and this measurement is consistent, then the on-hand inventory record might be adjusted. This approach may provide greater confidence that the on-hand inventory record was incorrect. Alternatively, the metrics engine may include rules for "weighing" different types of data and/or data sources, such as, for example, not requiring any repeatability when data from a reliable source indicates a discrepancy between an on-hand inventory record and a measured/calculated quantity. At block 414, the on-hand inventory record(s) may be adjusted if the metrics engine is satisfied.

In summary, in one preferred form, the system includes two sensor types collecting data at an inventory location, such as a shelf in a shopping facility. The first sensor type is generally in the form of weight sensors to determine the quantity of the merchandise at the shelf. The second sensor type is generally in the form of a mobile robot that moves up and down the aisles of the shopping facility. The mobile robot systematically collects data on merchandise at numerous shelves, such as by reading barcodes or by capturing images of the merchandise at the shelves. The captured images may then be compared to images in a product database, which contains image and other data regarding the length, width, height, and weight of individual products/merchandise items. In this form, each merchandise type is assigned a specific inventory location in the store, i.e., the inventory locations are precalibrated. In this form, the shopping facility includes a planogram indicating the placement of products on the shelves.

In this manner, by comparing the images from the second sensor, the control circuit can determine whether the correct product is on the correct shelf in the shopping facility. If not, the shelf can be restocked with the correct products. For example, the control circuit may transmit a notification or alert to the mobile device of a shopping facility employee to indicate that incorrect products on the shelf need to be replaced.

Further, in this preferred form, it is contemplated that the control circuit is remote from the two sensors and that the two sensors are in wireless communication with the remote control circuit. In turn, the control circuit is communicatively coupled to the product database (containing barcodes and/or images of merchandise items) and to an inventory database (containing on-hand inventory records with the quantities of merchandise items). Preferably, the system makes use of cloud computing platforms and cloud databases. The control circuit accesses the product database to determine and verify the merchandise at a particular shelf, i.e., by comparing the mobile robot sensor readings (images/barcodes) to those in the product database. The control circuit also accesses the inventory database to determine and verify merchandise quantity, i.e., it compares the quantity of merchandise items determined by the weight sensors with the quantity indicated in the inventory database. If the quantity detected on the shelf does not match the quantity indicated in the inventory database, then the inventory record in the database may be updated. When the detected quantity is below a certain minimum threshold, the control circuit may transmit a notification or alert to the mobile device of a shopping facility employee to restock that particular shelf.

Figure 6:
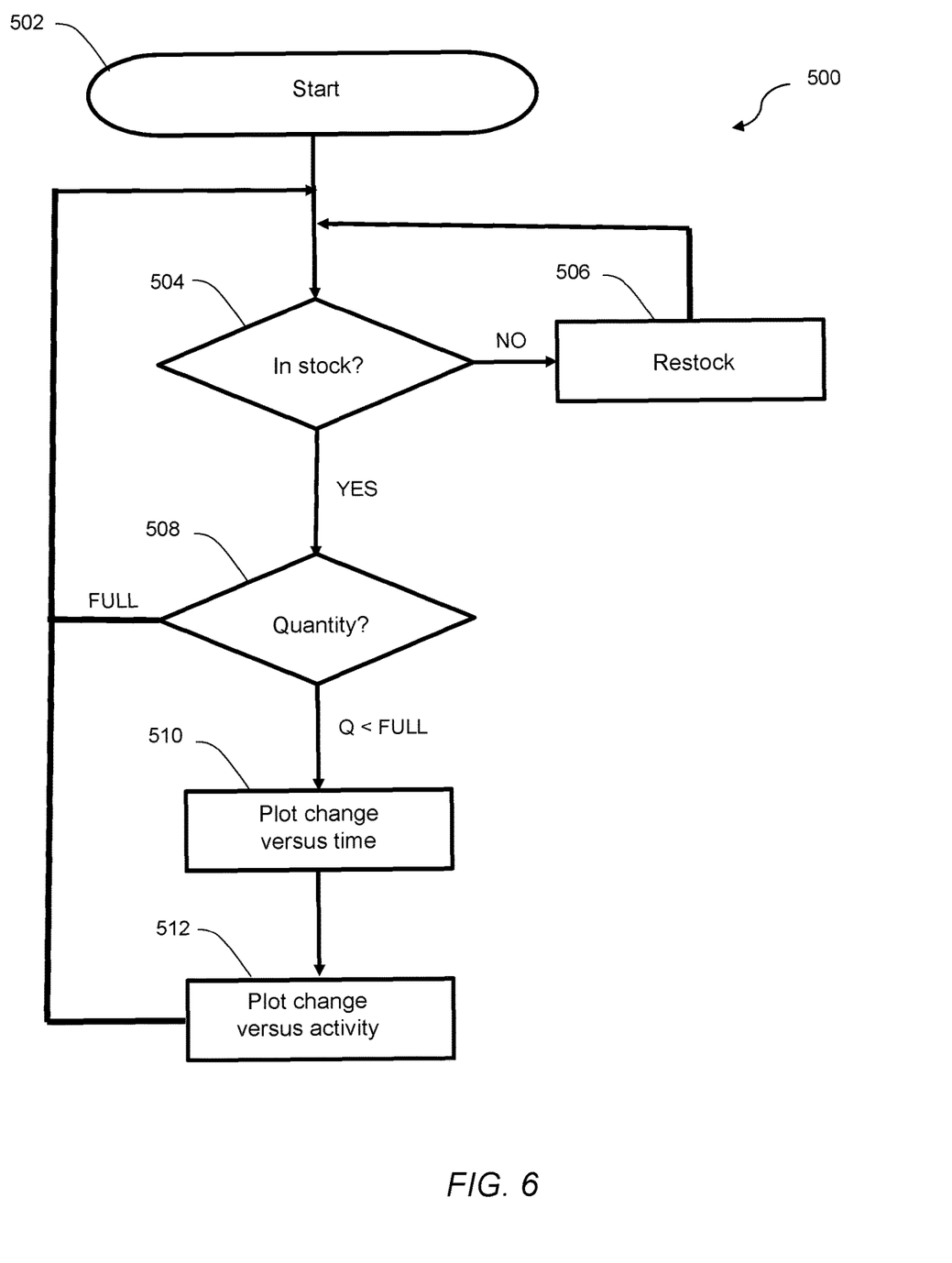
FIG. 6 is a flow diagram in accordance with several embodiments.

Referring to FIG. 6, there is shown a process 500 that may use some of the components and steps described in the above systems and processes. The process 500 is an iterative process of monitoring and tracking inventory trends over time, including tracking changes in inventory level and restocking activity by sales associates. The process 500 may be less concerned with tracking exact inventory levels at any exact point in time, although inventory above a certain minimum level should be maintained.

At block 502, the process 500 is initiated. At block 504, a determination is made if the merchandise is in stock. This determination may be based on measurements and data from various input sources, such as the first sensor, second sensor, and additional data sources described above. In one form, it is contemplated that if any sensor or data source indicates that the merchandise is not in stock (or that the merchandise on hand falls below a certain minimum level), then restocking activity 506 is to be performed immediately or within a short time period. For example, the metrics engine described in process 400 may be "weighted" such that any sensor or data source suggesting "out of stock" merchandise triggers this restocking activity 506. In this form, it is contemplated that maintaining inventory in stock is an important concern.

At block 508, if the merchandise is in stock, a determination is made if the inventory is "full." Again, this determination may be based on measurements and data from various input sources, such as described above. In one form, if the inventory is "full," no further tracking of changes in inventory level or stocking activity is required.

Figure 7A:
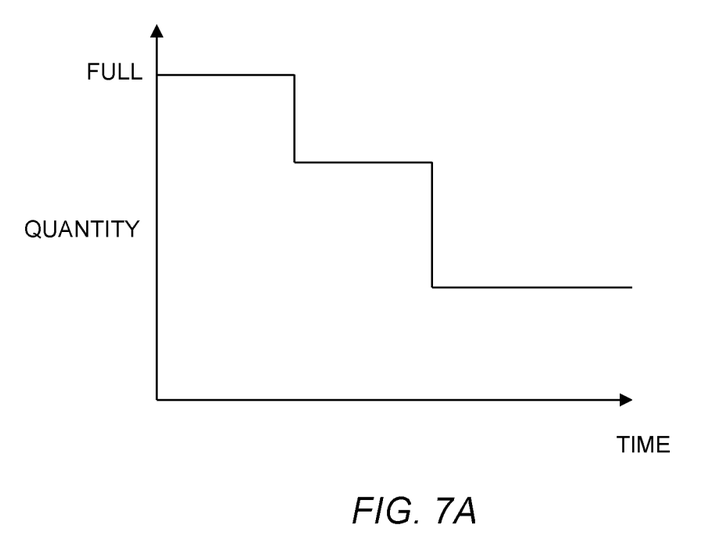
FIG. 7A is a graph showing quantity over time in accordance with several embodiments.

At block 510, if the quantity is at some intermediate level (between a minimum level requiring re-stocking and a full level), the inventory level of the merchandise may be plotted. FIG. 7A is a graph showing one example of plotting change of inventory over time. As can be seen in FIG. 7A, in one example, the inventory level started at a full level and then decreased over time. In this way, a general range of inventory levels may be tracked over time. The metrics engine may be set up to change on-hand inventory records if there is a significant divergence from measured/calculated inventory levels over a certain time period. The metrics engine may adjust the official on-hand store inventory record up or down a certain amount, which may lead to action by an employee (restocking or replenishing inventory). In one form, the exact on-hand inventory records at any specific time are less important (as long as inventory is above a predetermined minimum level) than the inventory being within a certain general range and/or less important than inventory trends over time.

Figure 7B:
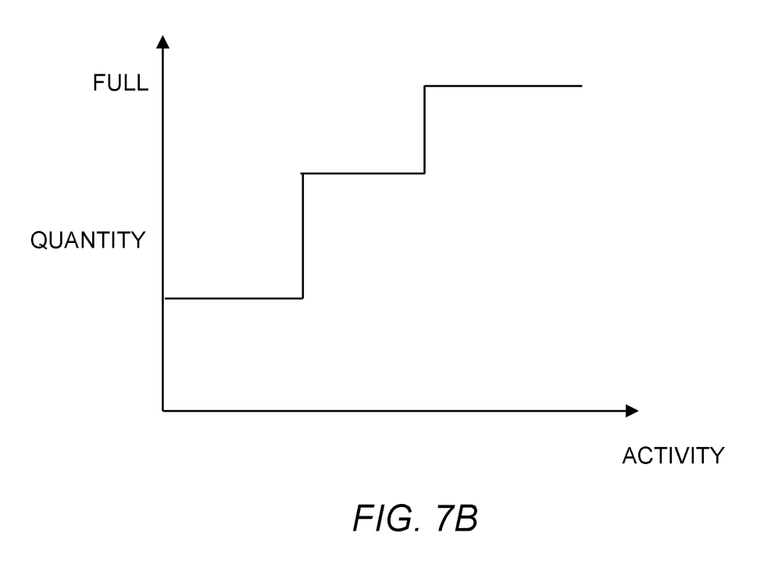
FIG. 7B is a graph showing restocking activity over time in accordance with several embodiments.

At block 512, the inventory level may be plotted as a function of restocking activity. FIG. 7B is a graph showing an example of plotting change of inventory versus restocking activity. As can be seen in FIG. 7B, in this example, the inventory level increases over time based on restocking activity to a full level. In this way, restocking activity may be monitored over time, and an increase or decrease in restocking activity may be implemented based on this data trend.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for monitoring inventory at various merchandise shelves in a shopping facility, the system comprising:
   a plurality of merchandise shelves disposed along aisles in a shopping facility;
   each merchandise shelf disposed adjacent an aisle and configured to contain a plurality of one type of merchandise item intended for a predetermined location on each merchandise shelf;
   a first type of sensor disposed at each merchandise shelf and configured to collect data regarding the presence of the type of merchandise item at each predetermined location on each merchandise shelf, the first type of sensor comprising a plurality of weight sensors arranged at a bottom surface of each merchandise shelf supporting merchandise items to collect weight data regarding merchandise items at each predetermined location of each merchandise shelf;
   a mobile robot including a second type of sensor, the mobile robot configured to move along the aisles of the shopping facility systematically and to capture image data of the type of merchandise item at each predetermined location on the plurality of merchandise shelves;
   a memory configured to store the image data collected by the second type of sensor;
   a product database including image information and weight information corresponding to the merchandise item intended for each merchandise shelf;
   an inventory database including an on-hand inventory record of the quantity of each type of merchandise item;
   a control circuit communicatively coupled to the sensors and in communication with the product and inventory databases, the control circuit configured to:
      compare the image data collected by the second type of sensor with the image information from the product database corresponding to merchandise items;
      verify that the image data from the second sensor of a merchandise item at each predetermined location corresponds to the image information of the merchandise item from the product database intended for the predetermined location according to a predetermined arrangement of types of merchandise items on the merchandise shelves;
      calculate a quantity of inventory at each predetermined location of a merchandise shelf based on the total weight of merchandise items at each predetermined location measured by the first type of sensor and based on the known weight of an individual merchandise item from the product database;
      compare the on-hand inventory record to the calculated quantity of inventory at each predetermined location; and
      adjust the on-hand inventory record to the calculated quantity.

2. The system of claim 1, wherein the first type of sensor comprises a plurality of individual strips defining a grid and extending along the bottom surface of each merchandise shelf.

3. The system of claim 1, wherein the second type of sensor comprises a scanning device including at least one of an optical sensor, an image recognition device, or a text capture device configured to read corresponding image data.

4. The system of claim 1, wherein the control circuit is configured to:
   compare the image data collected by the second type of sensor at the plurality of merchandise shelves with the image information of the merchandise item from the product database;
   determine if any image data at the predetermined locations correspond to the image information of the merchandise item from the product database; and
   determine that the merchandise item is located at a predetermined location other than or in addition to the intended predetermined location.

5. The system of claim 4, wherein:
the control circuit is configured to:
compare the images captured by the second type of sensor at the plurality of merchandise shelves with at least one image of a merchandise item from the product database; and determine if any images at the plurality of merchandise shelves correspond to the at least one image of the merchandise item from the product database to identify and locate merchandise items that are not in their intended predetermined location according to the predetermined arrangement of types of merchandise items.

6. The system of claim 1, wherein the predetermined arrangement of types of merchandise items on the merchandise shelves comprises a planogram.

7. The system of claim 1, wherein the control circuit is configured to:
compare the calculated quantity of inventory at each predetermined location to a predetermined minimum threshold; and
transmit an alert for restocking the merchandise item at the predetermined location.

8. The system of claim 1, wherein the control circuit is configured:
to receive additional data from one or more sources other than the first and second types of sensors regarding the inventory of the merchandise item intended for each predetermined location;
to compare the on-hand inventory record to the additional data regarding the inventory of the merchandise item; and
to adjust the on-hand inventory record based on the additional data.

9. The system of claim 8, wherein the additional data comprises at least one of: data from handheld scanners reading information regarding the merchandise item, imaging data from imaging equipment mounted at or near a predetermined location, sales or receipts of the merchandise item intended for the predetermined location, and feedback from customers regarding the quantity of the merchandise item at the predetermined location or the absence of the merchandise item at the predetermined location.

10. The system of claim 1, further comprising a visual alert indicator actuated by the control circuit when the calculated quantity of inventory at the predetermined location is below a predetermined amount.

11. A method for monitoring inventory at various merchandise shelves in a shopping facility, the method comprising:
providing a plurality of merchandise shelves disposed along aisles in a shopping facility;
depositing a plurality of one type of merchandise item at a predetermined location on each merchandise shelf adjacent an aisle;
by a first type of sensor, collecting data regarding the presence of the type of merchandise item at each predetermined location on each merchandise shelf, the first type of sensor comprising a plurality of weight sensors arranged at a bottom surface of each merchandise shelf supporting merchandise items to collect weight data regarding merchandise items at each predetermined location of each merchandise shelf;
by a mobile robot including a second type of sensor, moving along the aisles of the shopping facility systematically and capturing image data of the type of merchandise item at each predetermined location on the plurality of merchandise shelves;
storing the image data collected by the second type of sensor in a memory;
storing, in a product database, image information and weight information corresponding to the merchandise item intended for each predetermined location of each merchandise shelf;
storing, in an inventory database, an on-hand inventory record of the quantity of the merchandise item;
by a control circuit:
comparing the image data collected by the second type of sensor with image information of the merchandise item from the product database;
verifying that the image data from the second type of sensor corresponds to the image information of the merchandise item from the product database intended for the predetermined location according to a predetermined arrangement of types of merchandise items on the merchandise shelves; and
calculating a quantity of inventory at each predetermined location based on the total weight of merchandise items at the predetermined location measured by the first type of sensor and based on the known weight of an individual merchandise item from the product database;
comparing the on-hand inventory record to the calculated quantity of inventory at each predetermined location; and
adjusting the on-hand inventory record to the calculated quantity.

12. The method of claim 11, further comprising, by the control circuit:
comparing the images captured at the plurality of merchandise shelves with at least one image of the merchandise item from the product database;
determining if any images at the predetermined locations correspond to the at least one image of the merchandise item from the product database; and
determining that the merchandise item is located at a predetermined location other than or in addition to the intended predetermined location.

13. The method of claim 11, further comprising, by the control circuit:
receiving additional data from one or more sources other than the first and second types of sensors regarding the inventory of the merchandise item intended for a predetermined location;
comparing the on-hand inventory record to the additional data regarding the inventory of the merchandise item; and
adjusting the on-hand inventory record based on the additional data.

14. The method of claim 13, wherein the additional data comprises at least one of: data from handheld scanners reading information regarding the merchandise item, imaging data from imaging equipment mounted at or near a predetermined location, sales or receipts of the merchandise item intended for the predetermined location, and feedback from customers regarding the quantity of the merchandise item at the predetermined location or the absence of the merchandise item from the predetermined location.

15. The method of claim 11, further comprising:
repeating, a predetermined number of times, the steps of collecting data by the first type of sensor, collecting identification data by the second type of sensor, storing image data, comparing image data, verifying image data, calculating the quantity of inventory, communicating with the inventory database, and comparing the on-hand inventory record to the calculated quantity of inventory at each predetermined location; and
by the control circuit, determining if the on-hand inventory record is different from the calculated quantity each time and adjusting the on-hand inventory record.

* * * * *